United States Patent [19]

Mewshaw

[11] Patent Number: 5,541,199
[45] Date of Patent: Jul. 30, 1996

[54] CHROMAN-2-YLMETHYLAMINO DERIVATIVES

[75] Inventor: Richard E. Mewshaw, South Brunswick, N.J.

[73] Assignee: American Home Products Corporation, Madison, N.J.

[21] Appl. No.: 460,168

[22] Filed: Jun. 2, 1995

[51] Int. Cl.$^6$ .................. C07D 493/02; C07D 498/02; C07D 405/12; C07D 413/12

[52] U.S. Cl. .................. 514/314; 514/272; 514/275; 514/375; 514/379; 514/414; 514/422; 514/444; 514/456; 544/297; 546/153; 546/157; 546/176; 546/177; 548/217; 548/241; 548/454; 548/525; 549/60; 549/399

[58] Field of Search .................. 544/297; 546/153, 546/157, 176, 177; 548/217, 241, 454, 525; 549/60, 399; 514/272, 275, 314, 375, 379, 414, 422, 444, 456

[56] References Cited

U.S. PATENT DOCUMENTS

| | | | |
|---|---|---|---|
| 4,321,270 | 3/1982 | Sundeen | 424/267 |
| 5,126,367 | 6/1992 | Stack et al. | 514/452 |
| 5,137,901 | 8/1992 | Junge et al. | 514/373 |
| 5,318,988 | 6/1994 | Schohe-Loop et al. | 514/458 |
| 5,371,094 | 12/1994 | Heine et al. | 514/323 |

FOREIGN PATENT DOCUMENTS

| | | |
|---|---|---|
| 0325964 | 8/1989 | European Pat. Off. . |
| 0334429 | 9/1989 | European Pat. Off. . |
| 0369874 | 5/1990 | European Pat. Off. . |
| 9505383 | 2/1995 | WIPO . |

OTHER PUBLICATIONS

Indian Journal of Chemistry, 20B, 12, 1063–1067, Dec. 1981.

*Primary Examiner*—David Buttner
*Attorney, Agent, or Firm*—Richard K. Jackson

[57] ABSTRACT

Compounds of the formula:

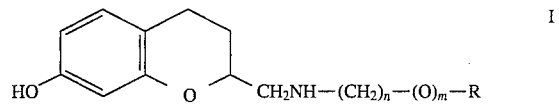

in which n is one of the integers 1, 2, 3, or 4; m is one of the integers 0 or 1; R is

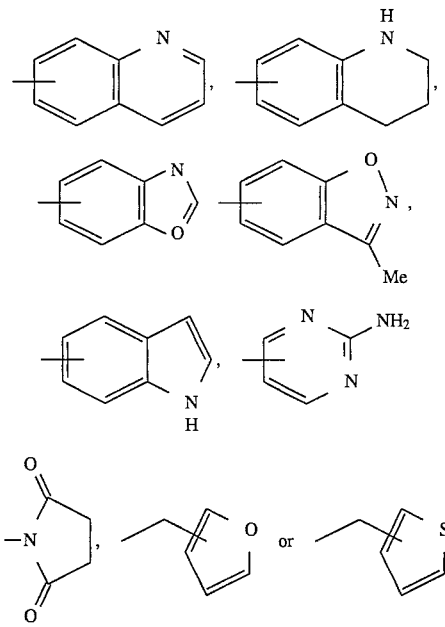

or a pharmaceutically acceptable salt thereof, are inhibitors of dopamine synthesis and release, useful in the treatment of schizophrenia, Parkinson's Disease, Tourette's Syndrome, alcohol addiction, cocaine addiction, and addiction to analagous drugs.

13 Claims, No Drawings

CHROMAN-2-YLMETHYLAMINO DERIVATIVES

BACKGROUND OF THE INVENTION

Efforts to induce antipsychotic activity with dopamine autoreceptor agonists have been successful (Corsini et al. Adv. Biochem. Psychopharmacol 16, 645–648, 1977; Tamminga et al. Science 200, 567–568, 1978; and Tamminga et al. Psychiatry 398–402, 1986). A method for determining intrinsic activity at the dopamine $D_2$ receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

DESCRIPTION OF THE INVENTION.

In accordance with this invention, there is provided a group of compounds which are useful antipsychotic agents. The compounds of this invention are essentially free from extrapyramidal side effects (EPS). The compounds of this invention are selective autoreceptor agonists, functioning primarily to activate only autoreceptors versus postsynaptic $D_2$ dopamine receptors). As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing a well as inhibition of dopamine synthesis and release and therefore provide a means of controlling hyperactivity of the dopaminergic systems.

More specifically, the compounds of this invention are depicted by the following Formula I:

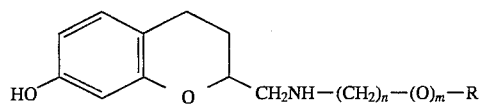

in which
n is one of the integers 1, 2, 3, or 4;
m is one of the integers 0 or 1;
R is

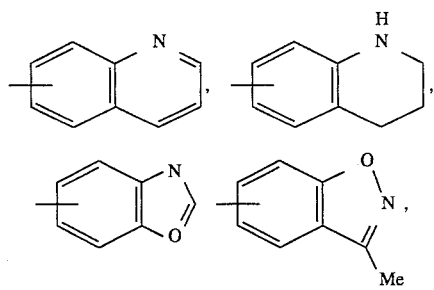

or a pharmaceutically acceptable salt thereof.

The pharmaceutically acceptable salts are those derived from such organic and inorganic acids as: acetic, lactic, citric, fumaric, tartaric, succinic, maleic, malonic, oxalic, hydrochloric, hydrobromic, phosphoric, nitric, sulfuric, methanesulfonic, methylbenzene sulfonic, and similarly known acceptable acids.

The compounds of Formula I are prepared by the overall sequence as follows:

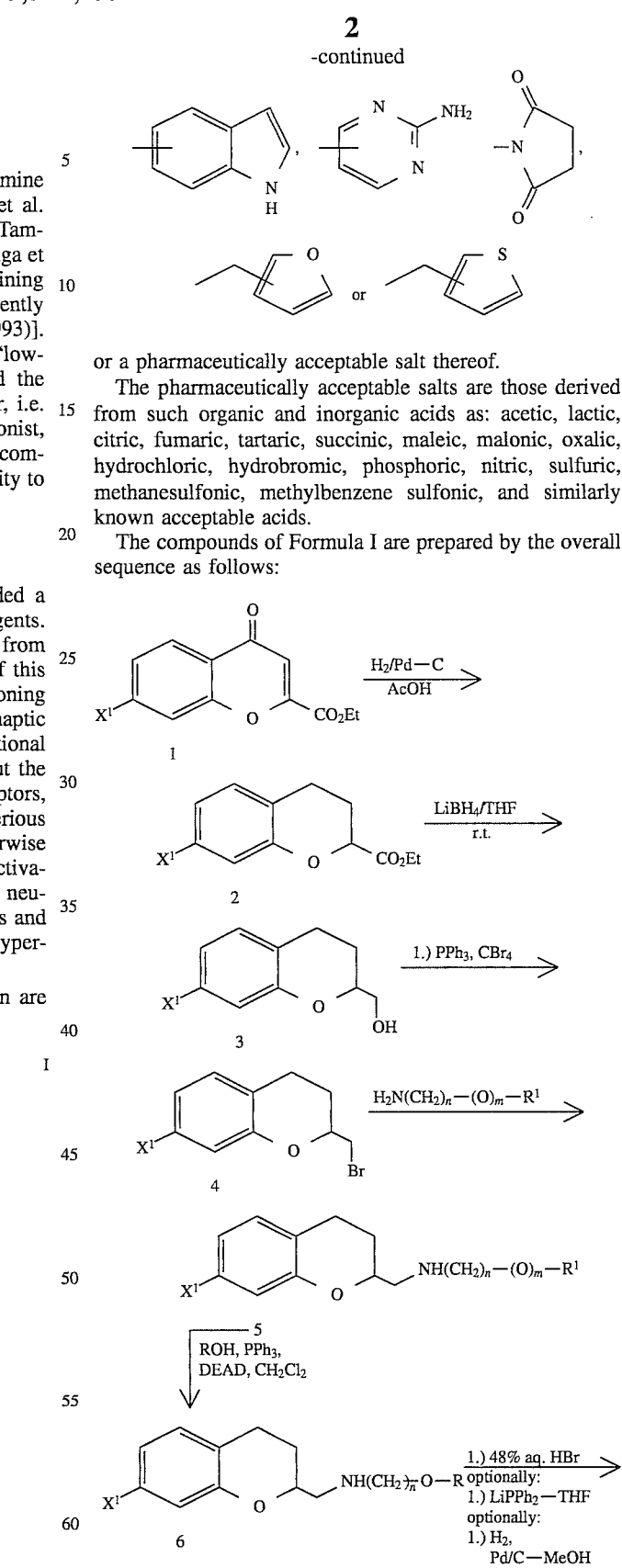

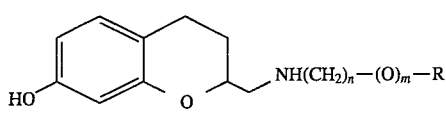

7

In this reaction sequence, $X^1$ is protected oxygen in which the protecting group is methyl, benzyl, and the like, known oxygen protecting groups. The final step of the reaction sequence, from compounds 5 or 6 to 7, involves deprotection of oxygen to provide the hydroxy group in 7-position of the benzopyran ring. The group $R^1$ is hydrogen or R (as defined above). The reaction sequence followed when $R^1$ is hydrogen and m is 1, proceeds via compound 6, whereas deprotection of compound 5, when $R^1$ is R and m is 1, proceeds directly to compound 7 by deprotection.

Specific exemplification of the production of representative compounds of this invention is given in the following procedures:

Intermediate 1

Ethyl (R,S)-3,4-Dihydro-7-methoxy-2H-1-benzopyran-2-carboxylate

A solution of ethyl 7-methoxy-4-oxo-4H-1-benzopyran-2-carboxylate [prepared from 1-hydroxy-5-methoxy-acetophenone according to Appleton et al. J. Med. Chem.20, 371–379, (1989)]in acetic acid (200 mL) was hydrogenated over 10% palladium on carbon at room temperature at 50 psi for 5 days. The reaction mixture was filtered through celite and the solvent was removed under vacuum. The product crystallized and was then triturated with 1:1 ethyl acetate-hexane to afford 20 g (72% yield) of product, mp 63°–64° C.; MS (EI) m/e 236 (M+).

Elemental Analysis for $C_{13}H_{16}O_4$ Calc'd: C, 66.09; H, 6.83 Found: C, 65.65; H, 6.76

Intermediate 2

(R,S)-3,4-Dihydro-7-methoxy-2H-1-benzopyran-2-methanol

To a solution of (R,S)-3,4-dihydro-7-methoxy-2H-1-benzopyran-2-carboxylic ethyl ester (20 g) was dissolved in tetrahydrofuran (215 mL) and a 2.0M solution of lithium borohydride (100 mL, 0.20 moles) was added over 5 h. After two hours the reaction was complete and the excess lithium borohydride was destroyed by the cautious addition of methanol. The reaction mixture was then diluted with ethyl acetate and washed with water. The organic layer separated and dried under vacuum to afford 16 g (96% yield) of a clear oil: IR (CDCl$_3$) 3600, 3450, 2920, 1620, 1585, and 1510 cm$^{-1}$; MS (EI) m/e, 194 (M+); $^1$H NMR (CDCl$_3$) δ1.75–1.94 (2H, m), 2.08 (1H, bs), 2.67–2.84 (2H, m), 3.74–3.86 (2H, m), 3.76 (3H, s), 4.09 (1H, m), 6.40 (1H, d, J=2.6 Hz), 6.46 (1H, dd, J=8.35, 2.64 Hz), 6.94 (1H, d, J=8.35 Hz).

Intermediate 3

(R,S)-3,4-Dihydro-7-(phenylmethoxy)-2H-1-benzopyran-2-methanol

This compound was prepared from (R,S)-3,4-dihydro-7-(phenylmethoxy)-2H-1-benzopyran-2-carboxylic ethyl ester [Cohen et al. J. Med. Chem. 32, 1842–1860, (1989)]by the procedure described in Example 2 in 98% yield as a yellow oil: MS (EI) m/e 270 (M+); $^1$H NMR (DMSO-d$_6$) δ1.57–1.67 (1H, m), 1.92–1.98 (1H, m), 2.48–2.73 (2H, m), 3.51–3.61 (2H, m), 4.74 (1H, t, J=5.71 Hz), 5.02 (2H, s), 6.36 (1H, d, J=2.64), 6.46 (1H, dd, J=8.35, 2.64 Hz), 6.92 (1H, d, J=8.35 Hz), 7.28–7.41 (5H, m).

Intermediate 4

(R,S)-3.4-Dihydro-7-methoxy-2H-1-benzopyran-2-methylbromide

To a solution of (R,S)-3,4-dihydro-7-methoxy-2H-1-benzopyran-2-methanol (3.14 g, 16.2 mmol) and carbontetrabromide (9.13 g, 28 mmol) in of methylene chloride (50 ml) was slowly added a solution of triphenylphosphine (7.21g, 27.5 mmol) in methylene chloride (50 mL) at 0° C. The reaction was allowed to warm to room temperature and stirred for 12 h then poured into water (150 mL) and extracted with methylene chloride (300 mL), dried and the solvent evaporated. Purification by chromatography (15% ethyl acetate/hexanes) afforded 3.16 g (75% yield) of a clear oil: IR (film) 2920, 1620, 1580, 1505, 1440, and 1160 cm-1; MS (EI) m/e, 258 (M+), 256 (M+); $^1$H NMR (CDCl$_3$) δ1.84–1.93 (1H, m), 2.11–2.18 (1H, m), 2.72–2.80 (2H, m), 3.52 (1H, dd, J=10.54, 5.93 Hz), 3.59 (1H, dd, J=10.54, 5,49 Hz), 3.75 (3H, s), 4.18–4.24 (1H, m), 6.40 (1H, d, J=2.42 Hz), 6.45 ( 1H, dd, J=8.35, 2.64 Hz), 6.94 (1H, d, J=8.35 Hz).

Intermediate 5

(R.S)-3,4-Dihydro-7-(benzloxy)-2H-1-benzopyran-2-methylbromide

This compound was prepared from (R,S)-3,4-dihydro-7-(benzyloxy)-2H-1 -benzopyran-2-methanol according to the procedure in Example 4 in 60% yield as a white solid, mp 76°–78° C.

Elemental analysis for $C_{17}H_{17}BrO_2$ Calc'd: C, 61.28; H, 5.14. Found: C, 61.26; H, 5.04

Intermediate 6

3-(7-Methoxy-chroman-2-ylmethyl-amino)-propanol

A mixture of (R,S)-3,4-dihydro-7-methoxy-2H1-benzopyran-2-methyl-bromide (12.8 g, 49 mmol) and 1-amino-3-propanol (10 eq) were heated to 100 ° C. for 2 hrs. The reaction mixture was washed with water (750 mLs) and extracted with methylene chloride (3×500 ml). The organic layer was dried over anhydrous magnesium sulfate, filtered, and the solvent evaporated to afford 11.3 g of desired product (92%). The oxalate salt was prepared from methanol, mp 180°–190° C.

Elemental analysis for $C_{14}H_{21}NO_3 \cdot C_2H_2O_4$ Calc'd: C, 56.30; H, 6.79; N, 4.10 Found: C, 55.92, H, 6.72: N, 4.10

Intermediate 7

3-[7-(Benzyloxy-chroman-2-ylmethyl)-amino]-propan-1-ol

This compound was prepared from (R,S)-3,4-dihydro-7-(benzyloxy)-2H-1 -benzopyran-2-methylbromide as described in the procedure for production of intermediate 6, in 98% yield as a pale yellow solid, mp 54°–55° C. IR (CHCl$_3$) 1560, 1500 and 1400 cm-1; MS (EI) m/e, 327 (M+).

Elemental analysis for $C_{20}H_{25}NO_3$ Calc'd: C, 73.37; H, 7.70; N 4.28 Found: C, 73.85; H, 7.84; N, 4.34

(7b)   7-Benzyloxy-chroman-2-ylmethyl)-(furan-2-ylmethyl)-amine.

This general procedure, utilizing 2-furanylmethylamine and (R,S)-3,4-dihydro-7-(benzyloxy)-2H-1-benzopyran-2-methylbromide as the reactants afforded 7 -benzyl-oxy-chroman-2-ylmethyl)-(2-methylfuranyl)-amine in 97% yield; IR (KBr) 1650, 1575, 1500 cm-1; MS (EI) m/e 349 (M+).

Intermediate 8

7-{3-[(7-methoxy-chroman-2-ylmethyl-amino]-propanoxy}-quinoline

To a solution of 3-(7-methoxy-chroman-2-ylmethyl-amino)-propanol (3.07 g, 13 mmol), 7-hydroxy quinoline (1.88 g, 13 mmol), triphenylphosphine (3.67 g, 14 mmol) in anhydrous tetrahydrofuran (50 mL) was slowly added a solution of diethylazodicarboxylate (2.44 g, 14 mmol) in tetrahydrofuran (10 ml). The reaction was allowed to stir for 3 hours and was then quenched with water, extracted with methylene chloride (150 mL) dried over anhydrous magnesium sulfate, filtered and the solvent removed under vacuum. Chromatography (2.5% MeOH -methylene chloride) afforded 2.72 g of the title compound (55% yield) which was converted to the monohydrate, dimaleate salt in tetrahydrofuran, mp 132°–134° C.

Elemental analysis for $C_{23}H_{26}N_2O_3 \cdot 2.0C_4O_4 \cdot 1.0H_2O$ Calc'd: C, 59.23; H, 5.77; N, 4.46 Found: C, 59.42; H, 5.53; N, 4.27

This general procedure utilizing 4-hydroxyindole afforded:

(8b)   [3-(1H-Indol-4-yloxy)-propyl]-(7-methoxy-chroman-2-ylmethyl)-amine oxalate salt (1:1) 0.33 hydrate, mp 206°–207.5° C., (67.3%).

Elemental analysis for $C_{19}H_{23}NO_2 \cdot C_2H_2O_4 \cdot 0.33H_2O$ Calc'd: C, 62.33; H, 6.25; N, 6.06 Found: C, 62.33; H, 6.02: N, 6.03

Intermediate 9

[3-(Benzoxazol-6-yloxy)-propyl]-(7-benzyloxy-chroman-2-ylmethyl)amine

To a solution of 3-[7-(benzyloxy-chroman-2-ylmethyl)-amino]-propan-1-ol (3.41 g, 10.4 mmol), 6-hydroxy-benzoxazole (1.83 g, 13.5 mmol), and triphenyl-phosphine (4.09 g, 15.6 mmol) in 80 mL of tetrahydrofuran was added diisopropylazodicarboxylate (3.15 g, 15.6 mmol) over 15 minutes. After stirring for 1 hour, the solvent was removed and the product purified by chromatography (ethyl acetate/methanol; 9–1) to afford 4.6 g (100% ) of the title compound as an orange oil. The hydrogen oxalate salt was prepared by adding an excess solution of oxalic acid in methanol to a warm solution of free base in methanol to afford a yellow solid: mp 127°–128° C.

Elemental analysis for $C_{27}H_{28}N_2O_4 \cdot 1.5(COOH)_2 \cdot 0.75H_2O$ Calc'd: C, 60.75; H, 5.52; N, 4.72 Found: C, 60.65; H, 5.32; N, 4.83

This general procedure utilizing 5-hydroxybenzoxazole, 6-hydroxy-3-methylbenzoisoxazole, isocytosine, succinimide afforded:

(9b)   [3-(Benzoxazol-5-yloxy)-propyl]-(7-benzyloxy-chroman-2-ylmethyl)-amine (77.6%); IR (2900, 1620, 1500, and 1403 cm-1; MS (EI) m/e, 444 (M+).

(9c)   [3-(3-Methyl-benzo[d]isoxazol-6-yloxy)-propyl]-(7-benzyloxy-chroman-2 -ylmethyl)-amine (76.6%): IR (film) 2900, 1620, 1580, and 1500 cm-1; MS (EI) m/e, 458 (M+).

(9d)   [3-(3-Amino-pyrimidin-4-yloxy)-propyl]-(7-benzyloxy-chroman-2-ylmethyl)amine (50.8% crude).

(9e) 1-{3-[(7-Benzyloxy-chroman-2-ylmethyl)-amino]-propyl}-pyrrolidine-2,5-dione (78.6%): IR (film) 2900, 1700, 1605, and 1500 cm$^{-1}$; MS (EI) m/e 408 (M+).

EXAMPLE 1

7-{3-[(7-Hydroxy-chroman-2-ylmethyl-amino]-propanoxy}-quinoline

A solution of 7-{3-[(7-methoxy-chroman-2-ylmethyl-amino]-propanoxy}-quinoline (2.19 g, 5.7 mmol) in 48% aqueous HBr was heated to reflux for 3 hours. The reaction mixture was then allowed to cool to room temperature and basified with 1N sodium hydroxide until pH 12. The basic reaction mixture was extracted with ethyl acetate (2×100 mL), dried over anhydrous magnesium sulfate, filtered, and the solvent removed under vacuum. Chromatography (7% methanol in methylene chloride containing 1% ammonium hydroxide) afforded 1.34 g of the title compound (63% yield). The corresponding oxalate salt was prepared by adding an excess of oxalic acid in warm ethanol to a solution of the free base in warm ethanol; mp 195.5°–196.5° C.

Elemental analysis for $C_{22}H_{24}N_2O_3 \cdot 2(COOH)_2$ Calc'd: C, 57.35; H, 5.18; N, 5.14 Found: C, 57.10; H, 5.56; N, 5.40

EXAMPLE 2

{7-Hydroxy-chroman-2-ylmethyl)-[3-(1,2,3,4-tetrahydro-quinolin-7-yloxy)-propyl]-amine 7-{3-[(7-Hydroxy-chroman-2-ylmethyl-amino]-propanoxy}-quinoline (1.1 g, 3.0 mmol) and $NiCl_2 \cdot 6H_2O$ (6 mmol) were dissolved in methanol (30 mL) and sodium borohydride (0.14 mol) was added in portions with stirring under cooling for 30 minutes, then allowed to warm to room temperature for 30 minutes. After removal of methanol, the black precipitate was dissolved in 1 N hydrochloric acid, the acidic solution was basified by the addition of concentrated ammonium hydroxide and extracted with diethylether. The organic layer was dried over anhydrous magnesium sulfate, filtered, and the solvent removed under vacuum. Chromatography (10% methanol-methylene chloride) afforded a brown oil (350 mg, 28.6%). The hemihydrate, monooxalate salt was prepared from methanol, mp 136°–139° C.

Elemental analysis for $C_{22}H_{28}N_2O_3 \cdot 2(COOH)_2 \cdot 0.5H_2O$ Calc'd: C, 56.43; H, 5.88; N, 5.11 Found: C, 57.33; H, 6.27; N, 5.49

EXAMPLE 3

2-{[3-(3-Methyl-benzo[d]isoxazol-6-yloxy)-propylamino]-methyl}-chroman-7-ol

A solution of [3-(3-methyl-benzo[d]isoxazol-6-yloxy)-propyl]-(7-benzyloxy-chroman-2-ylmethyl)amine (2.72 g, 5.9 mmol) in methanol (120 mL) containing 10% palladium on carbon (530 mg) was hydrogenated at 50 psi for 12 hours. The mixture was filtered through SOLKA FLOC®, washed with methanol, and the solvent evaporated. Chromatography (silica, 3% methanol in methylene chloride) afforded 1.5 g (68.7%) of a tan foam. The free base was dissolved in hot methanol (50 mL) and a solution of oxalic acid (1.5 g, 4 eq) in methanol (15 mL) was added. Upon cooling to room temperature an off-white solid precipitated and was filtered to afford 1.23 g of the oxalate salt of the title compound, mp 233°–235° C.

Elemental analysis for $C_{21}H_{24}N_2O_4 \cdot (COOH)_2$ Calc'd: C, 60.25; H, 5.72; N, 6.11 Found: C, 59.98; H, 5.86; N, 6.03

This general hydrogenolysis procedure was used to afford:

(3b) 2-{[3-(Benzoxazol-5-yloxy)-propylamino]-methyl}-chroman-7-ol oxalate salt (1:1) quarter hydrate, mp 162°–175° C. (dec), (66%).

Elemental analysis for $C_{20}H_{22}N_2O_4 \cdot (COOH)_2 \cdot 0.25H_2O$ Calc'd: C, 57.35; H, 5.18; N, 5.14 Found: C, 57.10; H, 5.56; N, 5.40

(3c) 2-{[3-(Benzoxazol-6-yloxy)-propylamino]-methyl}-chroman-7-ol oxalate salt (1:1) hemi hydrate, mp 193°–195° C., (48%).

Elemental analysis for $C_{20}H_{22}N_2O_4 \cdot (COOH)_2 \cdot 0.5H_2O$ Calc'd: C, 58.27; H, 5.56; N, 6.18 Found: C, 58.29; H, 5.46; N, 6.23

(3d) 1-{3-[(7-Hydroxy-chroman-2-ylmethyl)-amino]-propyl}-pyrrolidine-2,5-dione oxalate salt (1:1), 175°–177° C., (6.2%).

Elemental analysis for $C_{17}H_{22}N_2O_4 \cdot (COOH)_2$ Calc'd: C, 55.88; H, 5.92; N, 6.86 Found: C, 55.54; H, 5.86; N, 6.75

(3e) 2-{[3-(Amino-pyrimidin-4-yloxy)-propylamino]-methyl}-chroman-7-ol oxalate salt (2:3) hemihydrate, mp 193°–196° C., (63%).

Elemental analysis for $C_{17}H_{22}N_4O_3 \cdot 1.5(COOH)_2 \cdot 0.5H_2O$ Calc'd: C, 50.63; H, 5.52; N, 11.81 Found: C, 50.39; H, 5.33; N, 11.69

(3f) 2-{[(Furan-2-ylmethyl)-amino]-methyl}-chroman-7-ol oxalate salt three quarter hydrate (1:1), mp 169°–170° C.

Elemental analysis for $C_{15}H_{17}NO_3 \cdot C_2H_2O_4 \cdot 0.75H_2O$ Calc'd: C, 56.27; H, 5.69; N, 3.86 Found: C, 56.41; H, 5.39; N, 4.00

EXAMPLE 4

2-{3-(1H-Indol-4-yloxy)-propylamino]-methyl}-chroman-7-ol

To a solution of diphenylphosphine in dry tetrahydrofuran (25 mL) at 5° C. was added n-butyllithium (3.5 mL, 2.5 M). After 10 minutes a solution of [3-(1H-indol-4-yloxy)-propyl]-(7-methoxy-chroman-2-ylmethyl)-amine was added in tetrahydrofuran (10 mL) and allowed to stir for 2.5 days. The reaction was quenched with water and poured into diethyl ether (100 mL). The organic layer was separated, dried over anhydrous magnesium sulfate, filtered, and the solvent evaporated under vacuum. Chromatography (5% methanol-methylene chloride containing 1% ammonium hydroxide) afforded 280 mg (39.1%) of white foam. The 0.33 hydrate, oxalate salt was prepared from tetrahydrofuran, mp 199°–201° C.

Elemental analysis for $C_{21}H_{24}N_2O_3 \cdot (COOH)_2 \cdot 0.33H_2O$ Calc'd: C, 61.60; H, 5.99; N, 6.25 Found: C, 61.52; H, 5.72; N, 5.99

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given below.

| Example No. | $IC_{50}$(nM) Quin. | $IC_{50}$ (nM) D2 Spiper. | $IC_{50}$ (nM) $5-HT_{1a}$ | $IC_{50}$ (nM) $\alpha 1$ | Ratio |
|---|---|---|---|---|---|
| 1 | 0.8 | 206 | 13 | 26 | 258 |
| 2 | 1.34 | 209 | 1.51 | 50 | 156 |
| 3f | 2.25 | 40% | 417 | 3419 | — |
| 3c | 1.44 | 227 | 4.05 | 57 | 158 |
| 3b | 0.89 | 194 | 0.38 | 26 | 218 |
| 3a | 0.62 | 136 | 0.56 | 84 | 219 |
| 3d | 9.29 | 2175 | 303 | 277 | 234 |
| 3e | 1.11 | 310 | 154 | 70 | 279 |
| 4 | 1.33 | 211 | 1.28 | 12 | 159 |

Hence, the compounds of this invention effect the synthesis of the neurotransmitter dopamine and thus are useful in the treatment of dopaminergic disorders such as schizophrenia, Parkinson's Disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the formula:

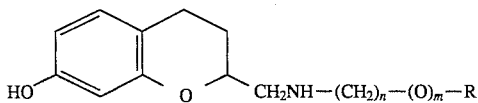

in which n is one of the integers 1, 2, 3,or 4;

m is one of the integers 0 or 1;

R is

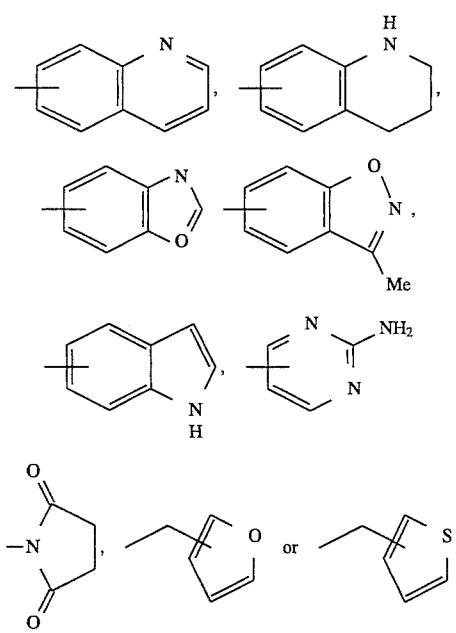

or a pharmaceutically acceptable salt thereof.

2. The compound of claim 1 which is 7-{3-[(7-hydroxy-chroman-2-ylmethyl-amino]-propanoxy}-quinoline or a pharmaceutically acceptable salt thereof.

3. The compound of claim 1 which is {7-hydroxy-chroman-2-ylmethyl)-[3-(1,2,3,4-tetrahydro-quinolin-7-yloxy)-propyl]-amine or a pharmaceutically acceptable salt thereof.

4. The compound of claim 1 which is 2-{[3-(3-methyl-benzo[d]isoxazol-6 -yloxy)-propylamino]-methyl}-chroman-7-ol or a pharmaceutically acceptable salt thereof.

5. The compound of claim 1 which is 2-{[3-(benzoxazol-5-yloxy)-propylamino]-methyl}-chroman-7-ol or a pharmaceutically acceptable salt thereof.

6. The compound of claim 1 which is 2-{[3-(benzoxazol-6-yloxy)-propylamino]-methyl}-chroman-7-ol or a pharmaceutically acceptable salt thereof.

7. The compound of claim 1 which is 1-{3-[(7-hydroxy-chroman-2-ylmethyl)-amino]-propyl}-pyrrolidine-2,5-dione or a pharmaceutically acceptable salt thereof.

8. The compound of claim 1 which is 2-{[3-(amino-pyrimidin-4-yloxy)-propylamino]-methyl}-chroman-7-ol or a pharmaceutically acceptable salt thereof.

9. The compound of claim 1 which is 2-{[(furan-2-ylmethyl)-amino]-methyl}-chroman-7-ol or a pharmaceutically acceptable salt thereof.

10. The compound of claim 1 which is 2-{[3-(1H-indol-4-yloxy)-propylamino]-methyl}-chroman-7-ol or a pharmaceutically acceptable salt thereof.

11. A pharmaceutical composition of matter comprising a compound of the formula:

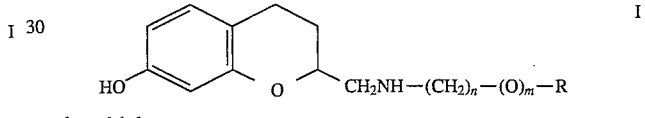

in which n is one of the integers 1, 2, 3,or 4;

m is one of the integers 0 or 1;

R is

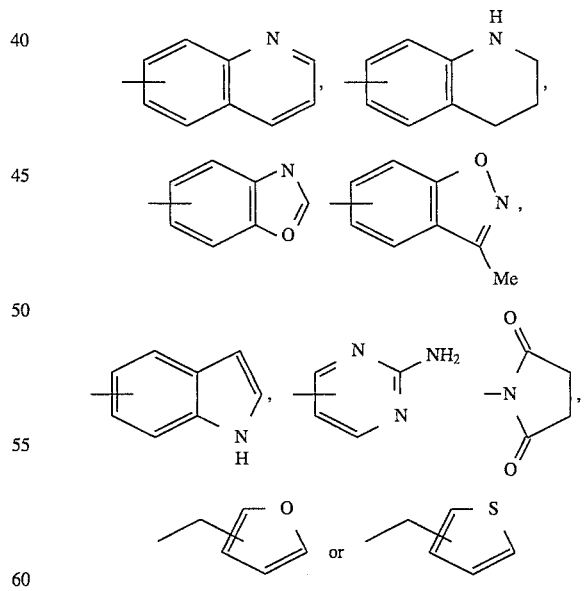

or a pharmaceutically acceptable salt thereof and a pharmaceutically acceptable carrier therefor.

12. A method for reducing dopamine synthesis and release in a patient suffering from hyperactivity of the dopaminergic systems, which comprises administering to said patient a compound of the formula:

11

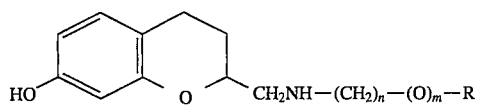

in which
n is one of the integers 1, 2, 3, or 4;
m is one of the integers 0 or 1;
R is

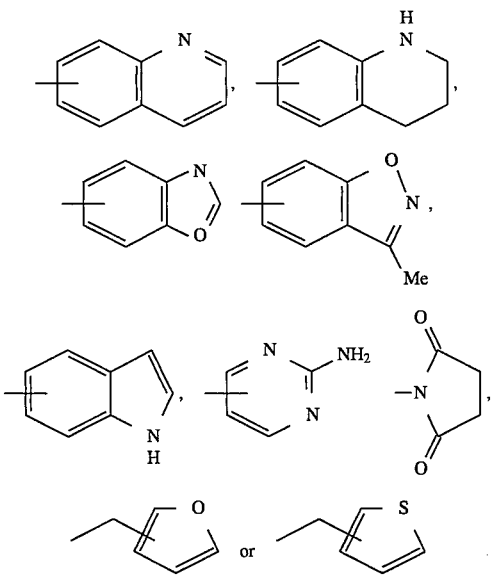

or a pharmaceutically acceptable salt thereof, in an amount sufficient to modulate the dopamine systems of the brain.

13. A method for treating schizophrenia which comprises administering to a patient suffering from schizophrenia, orally or parenterally, a compound of the formula:

12

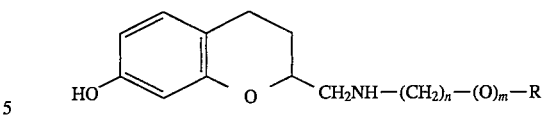

in which
n is one of the integers 1, 2, 3, or 4;
m is one of the integers 0 or 1;
R is

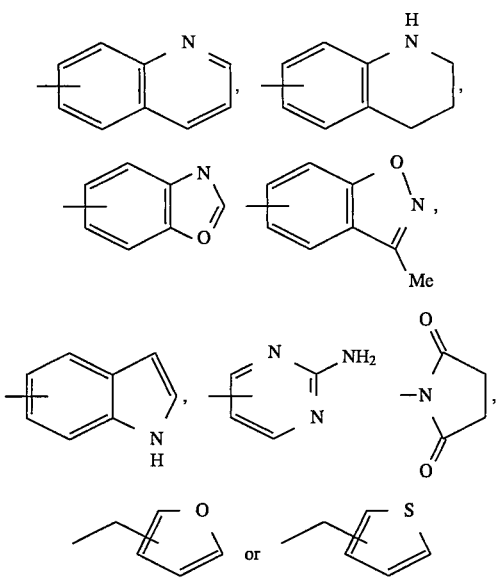

or a pharmaceutically acceptable salt thereof, in an amount sufficient to alleviate the symptoms of schizophrenia.

\* \* \* \* \*